United States Patent [19]

Heywang et al.

[11] Patent Number: 4,507,292
[45] Date of Patent: Mar. 26, 1985

[54] COMBATING PESTS WITH ARYL N-OXALYL-N-METHYL-CARBAMATES

[75] Inventors: Gerhard Heywang; Engelbert Kühle, both of Bergisch-Gladbach; Wolfgang Behrenz, Overath; Ingeborg Hammann, Muelheim; Bernhard Homeyer, Leverkusen, all of Fed. Rep. of Germany

[73] Assignee: Bayer Aktiengesellschaft, Leverkusen, Fed. Rep. of Germany

[21] Appl. No.: 461,368

[22] Filed: Jan. 27, 1983

[30] Foreign Application Priority Data

Feb. 13, 1982 [DE] Fed. Rep. of Germany ....... 3205195

[51] Int. Cl.³ .................... A01N 43/84; C07D 295/14
[52] U.S. Cl. ................. 514/183; 260/239 E; 260/239 A; 260/239 BF; 514/321; 514/320; 514/315; 514/415; 514/469; 514/234; 514/485; 544/58.4; 544/148; 544/153; 544/158; 544/163; 544/168; 544/374; 544/376; 544/377; 544/386; 546/196; 546/197; 546/206; 546/207; 546/226; 548/517; 548/525; 548/526; 548/530; 549/378; 549/435; 549/438; 549/448; 549/452; 549/470; 560/29; 560/31; 560/32
[58] Field of Search .............. 560/32, 29, 31, 27; 549/470, 378, 435, 448, 438, 452; 260/239 E, 239 AL, 239 BF; 546/196, 207, 197, 206, 226; 548/525, 517, 526, 530; 544/148, 153, 158, 163, 168, 58.4, 376, 377, 386, 374; 424/244, 246, 248.52, 248.54, 248.55, 250, 267, 274, 282, 285, 300

[56] References Cited

U.S. PATENT DOCUMENTS 3,393,224 7/1968 Brookes et al. ................... 560/25
3,857,860 12/1974 Kuhle et al. ..................... 560/32 X

FOREIGN PATENT DOCUMENTS 22498 1/1981 European Pat. Off. ........... 549/470

OTHER PUBLICATIONS

Houbon Weyl, *Methoden der Organischen Chemie*, vol. 8, G. Thieme Stuttgart, 1952, p. 149, lines 3-4.

Primary Examiner—Richard A. Schwartz
Attorney, Agent, or Firm—Sprung, Horn, Kramer & Woods

[57] ABSTRACT

Aryl N-oxalyl-N-methyl-carbamates of the general formula

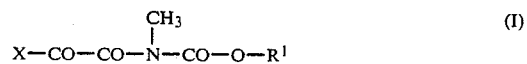

in which
X represents an alkoxy, alkenoxy, alkinoxy, aryloxy, alkylthio, alkenylthio, alkinylthio or arylthio radical, each of which may be optionally substituted, or represents a radical of the general formula —N $R^3R^4$, wherein $R^3$ and $R^4$ are identical or different and represent a hydrogen atom or an alkyl, alkenyl, alkinyl, cycloalkyl, cycloalkenyl or aryl radical, each of which may be optionally substituted,
or the radicals $R^3$ and $R^4$, together with the N atom to which they are bonded, form an optionally substituted heterocyclic ring, and
$R^1$ represents an aryl radical which is optionally substituted, are novel and find use as pesticides, especially for combating insects, acarids and nematodes.

7 Claims, No Drawings

COMBATING PESTS WITH ARYL N-OXALYL-N-METHYL-CARBAMATES

The present invention relates to certain N-oxalyl derivatives of methylcarbamates, to processes for their production and to their use as pest-combating agents.

It has already been disclosed that N-carboxylated aryl N-methyl-carbamates (see U.S. Pat. No. 4,014,923) and aryl N-chlorocarbonyl-N-methyl-carbamates (see DE-OS (German Published Specification) No. 2,142,496) have insecticidal properties. However, their action is not always completely satisfactory, particularly when low amounts are used.

The present invention now provides, as new compounds, the aryl N-oxalyl-N-methyl-carbamates of the general formula $$X-CO-CO-\underset{\underset{CH_3}{|}}{N}-CO-O-R^1 \quad (I)$$

in which
X represents an alkoxy, alkenoxy, alkinoxy, aryloxy, alkylthio, alkenylthio, alkinylthio or arylthio radical, each of which is optionally substituted, or represents a radical of the general formula $-NR^3R^4$,
wherein
R$^3$ and R$^4$ are identical or different and represent a hydrogen atom or an alkyl, alkenyl, alkinyl, cycloalkyl, cycloalkenyl or aryl radical, each of which may be optionally substituted,
or
the radicals R$^3$ and R$^4$, together with the N atom to which they are bonded, form an optionally substituted heterocyclic ring, and
R$^1$ represents an aryl radical which is optionally substituted.

The present invention further relates to a process for the production of a compound of formula (I) of the present invention, characterized in that an aryl N-chloroxalyl-N-methylcarbamate of the general formula $$R^1-O-CO-\underset{\underset{CH_3}{|}}{N}-CO-CO-Cl \quad (II)$$

in which
R$^1$ has the meaning given above,
is reacted with a nucleophile of the general formula $$HX \quad (III)$$

in which
X has the meaning given above, if appropriate in the presence of a diluent and/or if appropriate in the presence of an auxiliary base.

The present invention yet further relates to new intermediate compounds which are aryl N-chloroxalyl-N-methylcarbamates of the general formula $$R^1-O-CO-\underset{\underset{CH_3}{|}}{N}-CO-CO-Cl \quad (II)$$

in which
R$^1$ has the meaning given above.

The present invention also relates to a process for the production of an intermediate compound of formula (II) of the invention, characterized in that an aryl N-methylcarbamate of the general formula $$R^1-O-CO-\underset{\underset{CH_3}{|}}{N}-H \quad (IV)$$

in which
R$^1$ has the meaning given above, is reacted with oxalyl chloride, if appropriate in the presence of a diluent and/or if appropriate in the presence of an auxiliary base.

The compounds according to the invention are distinguished by good activity as insecticides, acaricides and nematocides.

It is extremely surprising that they have a favorable level of toxicity to warm-blooded animals and exhibit a more powerful action than the N-carboxylated N-methylcarbamates known from the prior art.

Preferred compounds of formula (I) according to the invention are those
in which
R$^1$ represents a phenyl, naphthyl, benzodioxolanyl, dihydrobenzofuranyl or indanyl radical, it being possible for these radicals to be substituted by alkyl, alkenyl, alkinyl, alkoxy, alkenoxy, alkinoxy, alkylthio, alkenylthio, alkinylthio, dialkylamino, halogenoalkyl, halogen, nitro, cyano, cycloalkyl, dioxanyl and/or dioxolanyl, and
X represents a radical of the general formula $$R^2-O-$$

wherein
R$^2$ represents a phenyl radical which can be optionally substituted by alkyl, alkenyl, alkinyl, halogenoalkyl, alkoxy, alkenoxy, alkinoxy, alkylthio, dialkylamino, halogen, nitro, cyano, cycloalkyl, formamidino, dioxanyl and/or dioxolanyl, or represents a C$_1$ to C$_6$ alkyl, C$_3$ to C$_6$ alkenyl or C$_3$ to C$_6$ alkinyl radical, these alkyl, alkenyl, and alkinyl radicals optionally being substituted by halogen, cyano, nitro, amino, hydroxy, alkoxy, alkylamino or dialkylamino, or X represents a radical of the general formula $$R^2-S-$$

wherein
R$^2$ has the meaning given immediately above,
or X represents a radical of the general formula $$\underset{R^4}{\overset{R^3}{\diagdown}}N-$$

wherein
R$^3$ and R$^4$ are identical or different and represent a hydrogen atom or a C$_1$ to C$_6$ alkyl, C$_3$ to C$_6$ alkenyl, C$_3$ to C$_6$ alkinyl, C$_3$ to C$_6$ cycloalkyl or C$_4$ to C$_6$ cycloalkenyl radical, each of which is optionally substituted by halogen, cyano, nitro, amino, hydroxyl, alkoxy- or dialkylamino, or represents a phenyl radical which is optionally substituted by $C_1$ to $C_4$ alkyl, halogen CN, $NO_2$ $C_1$ to $C_4$ alkoxy or $C_1$ to $C_4$ dialkylamino, or $R^3$ and $R^4$, together with the nitrogen atom to which they are bonded, form a ring, $R^3$ and $R^4$ then representing —$(CH_2)_n$— with n=2 to 6, or representing —$CH_2$—$CH_2$—Y—$CH_2$—$CH_2$—, wherein Y represents oxygen, sulphur, sulphoxide or sulphone, or nitrogen which is optionally substituted.

Particularly preferred compounds of the formula I are those in which $R^1$ represents a phenyl, 2-isopropylphenyl, 3-isopropylphenyl, 2-isopropoxyphenyl, 3,5-dimethyl-4-methyl-mercaptophenyl, 3-methyl-4-dimethylaminophenyl, 4-nitrophenyl, 2-allyloxyphenyl, 3-sec.-butyl-4-methyl-phenyl, 4-methyl-3-isopropylphenyl, 2-dimethylaminophenyl, 2-(1',3'-dioxolan-2'yl)-phenyl, 2-(4',5'-dimethyl-1',3'-dioxolan-2'-yl)-phenyl, naphth-1-yl, 4-(1,1-dimethylindanyl), 2,2-dimethylbenzodioxolanyl or 2,2-dimethyl-2,3-dihydrobenzo-furanyl-(7) radical, and X represents a methoxy, ethoxy, propoxy, isopropoxy, butoxy, isobutoxy, sec.-butoxy, tert.-butoxy, pentoxy, isopentoxy, hexoxy, isohexoxy, cyclopentoxy, cyclohexoxy, allyloxy, but-2-enyloxy, but-3-enyloxy, propargyloxy, but-2-inyloxy, but-3-inyloxy, 2-chloroethoxy, 2,2,2-trichloroethoxy, 2-fluoroethoxy, 2,2,2-trifluoroethoxy, 2-cyanoethoxy, 2-nitroethoxy, 2-methoxyethoxy, 2-dimethylaminoethoxy, phenoxy, 4-chlorophenoxy, 4-methylphenoxy, 4-methoxyphenoxy, 4-dimethylaminophenoxy, 1-naphthoxy, 2-naphthoxy or methylthio, ethylthio, butylthio, phenylthio, 4-chlorophenylthio, 4-methylphenylthio or amino, methylamino, dimethylamino, ethylamino, diethylamino, propylamino, isopropylamino, dipropylamino, diisopropylamino, butylamino, isobutylamino, dibutylamino, diisobutylamino, pyrrolidino, piperidino, morpholino, thiomorpholino, N-methylcyclohexylamino, N-phenylamino, N-methyl-N-phenylamino, diphenylamino, 4-methylphenylamino, N-methyl-N-4-methylphenylamino, N-methyl-N-4-methoxyphenylamino or N-methyl-N-4-chlorophenylamino radical.

Especially preferred compounds of the formula (I) which may be mentioned as those in which $R^1$ represents a 3-isopropylphenyl, 2-isopropoxyphenyl, 3,5-dimethyl-4-methylthiophenyl, 3-methyl-4-dimethylaminophenyl, 2-(1',3'-dioxolan-2'-yl)phenyl, naphth-1-yl, 4-(1,1-dimethylindanyl), 4-(2,2-dimethylbenzodioxolanyl) or 7-(2,2-dimethyl-2,3-dihydrobenzofuranyl) radical, and X represents a methoxy, ethoxy, 2,2,2-trichloroethoxy, 2,2,2-trifluoroethoxy, butoxy, allyloxy, propargyloxy, phenoxy, methylthio, phenylthio, dimethylamino, dibutylamino, piperidino or morpholino radical.

If 2,3-dihydro-2,2-dimethylbenzofuran-7-yl N-chloroxalyl-N-methylcarbamate and methanol are used as starting materials, of formulate (II) and (III), respectively, the course of the reaction according to the present invention for the production of compounds of formula (I) is illustrated by the following equation

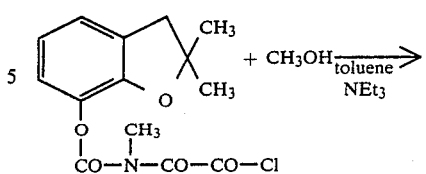

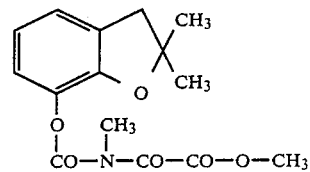

As indicated previously, the starting compounds of the formula (II) are new.

Preferred starting compounds for the production of compounds of the formula (II) are aryl N-methylcarbamates of the formula (IV), in which the radical $R^1$ has the meanings given the definitions of the preferred, particularly preferred and especially preferred compounds of the formula (I).

Suitable diluents for the preparation of the compounds according to the invention are inert organic solvents. These include ethers (such as diethyl ether, dioxane, or tetrahydrofuran), hydrocarbons (such as benzene or toluene), chlorinated hydrocarbons (such as methylene chloride, chloroform or chlorobenzenes) and furthermore nitriles, ketones and esters and mixtures of these solvents.

The auxiliary bases which may be added to the reaction mixture can be an acid-binding agent such as sodium carbonate, sodium bicarbonate or a tertiary organic base, for example, triethylamine or benzyldimethylamine. If X—H is an amine, this may also be employed as the base.

The reaction temperature can be varied within a relatively wide range. In general, the reaction is carried out at a temperature between 0° and 100° C.

Usually, the reactants are employed in equimolar amounts, but it is also possible to use one component in excess, although this has no substantial advantages.

The new intermediate compounds of the formula (II) are obtained by reacting aryl N-methylcarbamates of the formula (IV) with oxalyl chloride.

If 2,3-dihydro-2,2-dimethylbenzofuran-7-yl N-methylcarbamate is used as the starting material of formula (IV) the course of the reaction for the production of starting compounds of formula (II) is illustrated by the following equation:

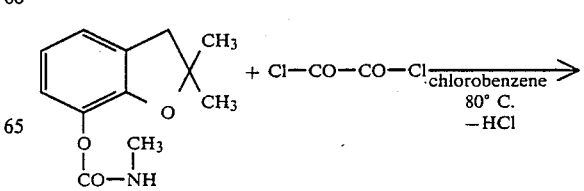

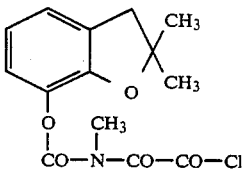

Suitable diluents for this reaction are inert organic solvents. These include ethers (such as diethyl ether, dioxane or tetrahydrofuran), hydrocarbons (such as benzene, toluene or xylene), chlorinated hydrocarbons (such as chloroform, dichloroethane or chlorobenzenes), and furthermore nitriles, ketones and esters, and mixtures of these solvents.

The hydrogen chloride formed in the reaction can be flushed out with gases, such as air or nitrogen, or escapes owing to the reaction temperature, or sodium carbonate, sodium bicarbonate or a tertiary organic base, such as triethylamine, benzyldimethylamine or N-N-dimethylaniline, is added to the reaction mixture, as an acid-binding agent.

The reaction temperature can be varied within a relatively wide range. In general the reaction is carried out at a temperature between 0° and 150° C., preferably between 60° and 130° C., when no acid-binding agents are added.

Usually, the reactants are employed in equimolar amounts, but it is also possible to use one component in excess, although this has no advantages.

The active compounds are well tolerated by plants, have a favorable level of toxicity to warm-blooded animals, and are suitable for combating arthropod pests, especially insects and arachnida, and nematodes, which are encountered in agriculture, in the forestry, in the protection of stored products and of materials, and in the hygiene field. They are active against normally sensitive resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp.,

*Hyaloma* spp., *Ixodes* spp., *Psoroptes* spp., *Chorioptes* spp., *Sarcoptes* spp., *Tarsonemus* spp., *Bryobia praetiosa, Panonychus* spp. and *Tetranychus* spp..

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichodorus spp..

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms.

The active compounds according to the invention can furthermore be present in their commercially available formulations, and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% and 1% by weight.

The compounds are employed in a customary manner appropriate for the use forms.

When used against pests harmful to health and pests of stored products, the active compounds are distinguished by an excellent residual action on wood and clay as well as a good stability to alkali on limed substrates.

The present invention also provides a pesticidal composition containing as active ingredient a compound of the present invention in admixture with a solid or liquefied gaseous diluent or carrier or in admixture with a liquid diluent or carrier containing a surface-active agent.

The present invention also provides a method of combating pests (in particular arthropods, especially insects or acarids, and nematodes) which comprises applying to the pests or to a habitat thereof, a compound of the present invention alone or in the form of a composition containing as active ingredient a compound of the present invention in admixture with a diluent or carrier.

The present invention further provides crops protected from damage by pests by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

I. PREPARATION OF THE COMPOUNDS OF THE FORMULA (I)

EXAMPLE 1

Methyl 2-[N-7-(2,3-dihydro-2,2-dimethylbenzofuranyl)-oxycarbonyl-N-methyl]-amino-2-oxo-ethanoate

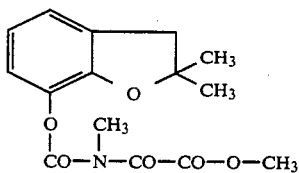

(1)

First 1 g of methanol and then 2.8 g of triethylamine were added dropwise to 8.7 g of 2,3-dihydro-2,2-dimethylbenzofuran-7-yl N-oxalyl-N-methylcarbamate in 20 ml of chlorobenzene, at room temperature. The mixture was stirred for a further 30 minutes and filtered, and the organic phase was washed twice with 10 ml of water. After it had been dried over sodium sulphate, the solvent was distilled off in vacuo, and the residue was a slightly brownish oil. 8 g (93%), $n_D^{20}$: 1.5324.

The following oxalic acid derivatives of carbamates of formula (I) were prepared in a corresponding manner:

$$R^1-O-CO-N(CH_3)-CO-CO-X \quad (I)$$

| Example Number | $R^1$ | X | Yield (%) | $n_D^{20}$ | Mp. (°C.) |
|---|---|---|---|---|---|
| 2 | 2,3-dihydro-2,2-dimethylbenzofuran-7-yl | —O—C$_2$H$_5$ | 100 | 1.5208 | |
| 3 | 2,3-dihydro-2,2-dimethylbenzofuran-7-yl | —O—C$_4$H$_9$ | 92 | 1.5150 | |
| 4 | " | —O—CH$_2$—CF$_3$ | 68 | 1.483 | |
| 5 | " | —O—CH$_2$—CCl$_3$ | 60 | | 75–78 |
| 6 | " | —O—CH$_2$—CH=CH$_2$ | 100 | 1.5242 | |
| 7 | " | —O—CH$_2$—C≡CH | 64 | 1.5281 | |
| 8 | " | —O—C$_6$H$_5$ | 58 | | 118–125 |
| 9 | " | —S—C$_6$H$_5$ | 90 | | 78–81 |
| 10 | " | —N(C$_4$H$_9$)$_2$ | 97 | 1.5171 | |
| 11 | " | —N(piperidinyl) | 84 | | 111–118 |
| 11a | " | —O—C$_6$H$_5$ (phenoxy) | 72 | | 122 |
| 12 | 2,6-dimethyl-4-(methylthio)phenyl | —O—CH$_3$ | 96 | | 66 |
| 13 | " | —O—C$_4$H$_9$ | 85 | | 68–74 |
| 14 | 1-naphthyl | —O—C$_4$H$_9$ | 86 | 1.5573 | |
| 15 | 2-isopropoxyphenyl | —O—CH$_3$ | 86 | 1.5072 | |

-continued $$R^1-O-CO-N(CH_3)-CO-CO-X \quad (I)$$

| | | | | |
|---|---|---|---|---|
| 16 | " | —O—C$_4$H$_9$ | 83 | 1.4992 |

II. PREPARATION OF THE STARTING COMPOUNDS

EXAMPLE 17

2,3-dihydro-2,2-dimethyl-benzofuran-7-yl N-chloroxalyl-N-methyl-carbamate 5.4 ml of oxalyl chloride were added dropwise to 12.2 g of 2,3-dihydro-2,2-dimethylbenzofuran-7-yl N-methyl-carbamate in 100 ml of chlorobenzene, and the mixture was then warmed slowly to 60° to 80° C., until the evolution of gas was complete (about 4 hours). The solution thus formed could be used for the reaction giving the compounds according to the invention. After the chlorobenzene had been distilled off in vacuo, 15 g of viscous oil remained, which, according to the gas chromatogram, consisted of 96% of the desired compound and 4% of chlorobenzene. The compound boiled at 161° C./0.01 mbar, without decomposing.

EXAMPLE 18

Phenyl N-chloroxalyl-N-methylcarbamate 151 g of phenyl N-methyl-carbamate were reacted with 127 of oxalyl chloride in 1 liter of chlorobenzene, analogously to the method of Example 17. 220 g (91%) of colorless oil of boiling point 142° C./0.01 mbar were obtained.

EXAMPLE 19

3,5-dimethyl-4-methylthio-phenyl N-chloroxalyl-N-methyl-carbamate 112.5 g of 3,5-dimethyl-4-methylthio-phenyl N-methyl-carbamate in 500 ml of chlorobenzene were reacted with 63.5 g of oxalyl chloride, analogously to Example 17. After the solvent had been evaporated, a crystalline product was obtained, which was washed with diisopropyl ether: 152 g (96%), melting point 100° to 104° C.

The following compounds were obtained analogously:

EXAMPLE 20

Yield 100%
M.p. 85°–90° C.

EXAMPLE 22

Yield 97%
M.p. 55°–65° C.

EXAMPLE 23

3-Methyl-4-dimethylamino-phenyl N-chloroxalyl-N-methylcarbamate hydrochloride 63.5 g of oxalyl chloride were added to 104 g of 3-methyl-4-dimethylaminophenyl N-methylcarbamate in 500 ml of chlorobenzene, analogously to the method of Example 17. The reaction mixture was heated at 60° C. for 4 hours. During this period an oily layer was deposited on the wall of the reaction vessel. The chlorobenzene was decanted and the residue was digested with diisopropyl ether.

60 g (40%) of a very hygroscopic colorless powder melting within a range of 52° to 69° C.

The pesticidal activity of the compounds of this invention is illustrated by the following biotest examples.

In these examples, the compounds according to the present invention are each identified by the number (given in brackets) of the corresponding preparative example.

EXAMPLE A

Myzus test
Solvent: 3 parts by weight of dimethylformamide

Emulsifier: 1 part by weight of alkylaryl polyglycol ether

To produce a suitable preparation of active compound, 1 part by weight of active compound was mixed with the stated amount of solvent and the stated amount of emulsifier, and the concentrate was diluted with water to the desired concentration.

Cabbage leaves (*Brassica oleracea*) which had been heavily infested with peach aphids (*Myzus persicae*) were treated by being dipped into the preparation of active compound of the desired concentration.

After the specified periods of time, the destruction in % was determined. 100% meant that all the aphids had been killed; 0% meant that none of the aphids had been killed.

In this test the following compounds, for example, showed a superior activity compared to the prior art: (1), (2), (3), (4), (5), (6), (7), (9), (11) and (11a).

EXAMPLE B

Doralis test (systemic action)
Solvent: 3 parts by weight of dimethylformamide
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Bean plants (*Vicia faba*) which had been heavily infested with the bean aphid (*Doralis fabae*) were each watered with 20 ml of the preparation of the active compound of the desired concentration in such a way that the preparation of the active compound penetrated into the soil without wetting the shoot. The active compound was taken up by the roots and passed to the shoot.

After the specified periods of time, the destruction in % was determined. 100% meant that all the aphids had been killed; 0% meant that none of the aphids had been killed.

In this test the following compounds, for example, showed a superior activity compared to the prior art: (1), (2), (3), (4), (5), (7), (9), (11) and (11a).

EXAMPLE C

Tetranychus test (resistant)
Solvent: 3 parts by weight of dimethylformamide
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Bean plants (*Phaseolus vulgaris*) which were heavily infested with the common spider mite or two-spotted spider mite (*Tetranychus urticae*) in all stages of development were treated by being dipped-into the preparation of the active compound of the desired concentration.

After the specified periods of time, the destruction in % was determined. 100% meant that all the spider mites had been killed; 0% meant that none of the spider mites had been killed.

In this test the following compound, for example, showed a superior activity compared to the prior art: (4).

EXAMPLE D

Test insect: *Myzus persicae* (root-systemic action)
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added, and the concentrate was diluted with water to the desired concentration.

The preparation of active compound was intimately mixed with soil. The concentration of the active compound in the preparation was of practically no importance, only the amount by weight of active compound per unit volume of soil, which was given in ppm (=mg/l) being decisive. The treated soil was filled into pots and these were planted with cabbage (*Brassica oleracea*). The active compound could in this way be taken up from the soil by the roots of the plants and transported into the leaves.

To demonstrate the root-systemic effect, exclusively the leaves were infested with the abovementioned test insects after 7 days. After a further 2 days, the evaluation was made by counting or estimating the dead insects. The root-systemic action of the active compound was deduced from the mortality figures. It was 100% if all the test insects had been killed and 0% if just as many test insects were still alive as in the case of the untreated control.

In this test the following compounds, for example, showed a superior action compared to the prior art: (1), (2), (3), (4), (5), (6), (9), (11) and (11a).

EXAMPLE E

Test insect: *Phaedon cochleariae* larvae (root-systemic action)
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added, and the concentrate was diluted with water to the desired concentration.

The preparation of active compound was intimately mixed with soil. The concentration of the active compound in the preparation was of practically no importance, only the amount by weight of active compound per unit volume of soil, which was given in ppm (=mg/l) being decisive. The treated soil was filled into pots and these were planted with cabbage (*Brassica oleracea*). The active compound could in this way be taken up from the soil by the roots of the plants and be transported into the leaves.

To demonstrate the root-systemic effect, exclusively the leaves were infested with the abovementioned test insects after 7 days. After a further 2 days, the evaluation was made by counting or estimating the dead insects. The root-systemic action of the active compound was deduced from the mortality figures. It was 100% if all the test insects had been killed and 0% if just as many test insects were still alive as in the case of the untreated control.

In this test the following compounds, for example, showed a superior action compared to the prior art: (1), (2), (3), (6), (11), (11a) (7), (4) and (9).

EXAMPLE F

Test insect: *Phorbia antiqua* maggots (in the soil)
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added, and the concentrate was diluted with the water to the desired concentration.

The preparation of active compound was initimately mixed with soil. The concentration of the active compound in the preparation was of particularly no importance, only the amount by weight of active compound per unit volume of soil, which was given in ppm (=mg/l) being decisive. The soil was filled into pots and the pots were left to stand at room temperature.

After 24 hours the test insects were introduced into the treated soil, and after a further 2 to 7 days the degree of effectiveness of the active compound was determined in % by counting the dead and live test insects. The degree of effectiveness was 100% if all the test insects had been filled and was 0% if just as many test insects were still alive as in the case of the untreated control.

In this test the following compounds, for example, showed a superior action compared to the prior art: (1), (2), (3), (5), (6), (10), (11), (11a), (4) and (9).

EXAMPLE G

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added, and the concentrate was diluted with water to the desired concentration.

The preparation of active compound was intimately mixed with soil which was heavily infested with the test nematodes. The concentration of the active compound in the preparation was of practically no importance, only the amount of active compound per unit volume of soil, which was given in ppm, being decisive. The treated soil was filled into pots, lettuce was sown in and the pots were kept at a greenhouse temperature of 27° C.

After four weeks, the lettuce roots were examined for infestation with nematodes (root galls), and the degree of effectiveness of the active compound was determined in %. The degree of effectiveness was 100% if infestation was completely avoided and was 0% if the infestation was just as high as in the case of the control plants in untreated soil which has been infested in the same manner.

In this test the following compounds, for example, showed a superior action compared to the prior art: (10).

EXAMPLE H

LT$_{100}$ test for Diptera
Test insects: *Musca domestica* (resistant)
Number of test insects: 25
Solvent: Acetone 2 parts by weight of active compound were taken up in 1,000 parts by volume of solvent. The solution thus obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remains uncovered until the solvent had completely evaporated. The amount of active compound per m$^2$ of filter paper varied with the concentration of the solution of active compound used. The stated number of test insects was then placed in the Petri dish and the dish was covered with a glass lid.

The condition of the test insects was continuously checked. The time which was necessary for a 100% knock-down effect was determined.

In this test the following compounds, for example, from the preparation examples showed a superior action compared to the prior art: (9), (11), (5) and (4).

It will be appreciated that the instant specification and examples are set forth by way of illustration and not limitation, and that various modifications and changes may be made without departing from the spirit and scope of the present invention.

We claim:

1. An aryl N-oxalyl-N-methylcarbamate of the formula

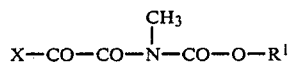

in which
R$^1$ represents a phenyl, naphthyl, benzodioxolanyl, dihydrobenzofuranyl or indanyl radical, the latter three radicals being attached via the aromatic ring thereof, the foregoing optionally being substituted by loweralkyl, loweralkenyl, loweralkinyl, loweralkoxy, loweralkenoxy, loweralkinoxy, loweralkylthio, loweralkenylthio, loweralkinylthio, diloweralkylamino, halogenoloweralkyl, halogen, nitro, cyano, cycloloweralkyl, dioxanyl and/or dioxolanyl, and X represents a radical of the formula

wherein
R$^3$ and R$^4$ are identical or different and represent a hydrogen atom or a C$_1$ to C$_6$ alkyl, C$_3$ to C$_6$ alkenyl, C$_3$ to C$_6$ alkinyl, C$_3$ to C$_6$ cycloalkyl or C$_4$ to C$_6$ cycloalkenyl radical, each of which is optionally substituted by halogen, cyano, nitro, amino, hydroxyl, loweralkoxy or diloweralkylamino, or represent a phenyl radical which is optionally substituted by C$_1$ to C$_4$ alkyl, halogen, CN, NO$_2$, C$_1$ to C$_4$ alkoxy or C$_1$ to C$_4$ dialkylamino, or R$^3$ and R$^4$, together with the nitrogen atom to which they are bonded, can also form a ring, R$^3$ and R$^4$ then representing —(CH$_2$)$_n$— with n=2 to 6, or representing —CH$_2$—CH$_2$—Y—CH$_2$—CH$_2$—, wherein
Y represents oxygen, sulphur, sulphoxide or sulphone, or nitrogen.

2. A compound according to claim 1, in which R$^1$ represents a 3-isopropylphenyl, 2-isopropoxyphenyl, 3,5-dimethyl-4-methylthiophenyl, 3-methyl-4- dimethylaminophenyl, 2-(1',3'-dioxolan-2'-yl)phenyl, naphth-1-yl, 4-(1,1-dimethylindanyl), 4-(2,2-dimethylbenzodioxolanyl) or 7-(2,2-dimethyl-2,3-dihydrobenzofuranyl) radical, and X represents a dimethylamino, dibutylamino, piperidino or morpholino radical.

3. A compound according to claim 1, in which:
R¹ is

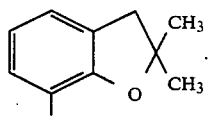

4. A compound according to claim 1, in which:
X is

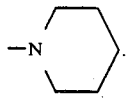

5. A compound according to claim 3, in which:
X is

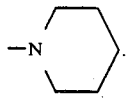

6. An arthropodicidal or nematocidal composition comprising an arthropodicidally or nematocidally effective amount of a compound according to claim 1 in admixture with a diluent.

7. A method of combating arthropods or nematodes comrising applying to the arthropods or nematodes, or to a habitat thereof, an arthropodicidally or nematocidally effective amount of a compound according to claim 1.

* * * * *